(12) United States Patent
Johnson

(10) Patent No.: US 12,376,511 B2
(45) Date of Patent: Aug. 5, 2025

(54) CONTROLLING AN AGRICULTURAL VEHICLE BASED ON SOIL DAMAGE SCORE

(71) Applicant: Deere & Company, Moline, IL (US)

(72) Inventor: Lee A. Johnson, Polk City, IA (US)

(73) Assignee: Deere & Company, Moline, IL (US)

( * ) Notice: Subject to any disclaimer, the term of this patent is extended or adjusted under 35 U.S.C. 154(b) by 869 days.

(21) Appl. No.: 17/581,297

(22) Filed: Jan. 21, 2022

(65) Prior Publication Data

US 2023/0232731 A1 Jul. 27, 2023

(51) Int. Cl.
A01B 79/00 (2006.01)
A01B 79/02 (2006.01)
G01N 33/24 (2006.01)

(52) U.S. Cl.
CPC .......... *A01B 79/005* (2013.01); *A01B 79/02* (2013.01); *G01N 33/24* (2013.01); *G01N 33/245* (2024.05)

(58) Field of Classification Search
CPC ....... A01B 76/00; A01B 79/005; A01B 79/02; A01B 63/24; A01B 69/008; G01N 33/04; G01N 33/24; G01N 33/245
See application file for complete search history.

(56) References Cited

U.S. PATENT DOCUMENTS

| | | | |
|---|---|---|---|
| 6,029,106 A | 2/2000 | Hale | |
| 6,041,582 A | 3/2000 | Tiede et al. | |
| 10,315,655 B2 | 6/2019 | Blank et al. | |
| 10,675,924 B2 | 6/2020 | Milburn, Jr. et al. | |
| 10,918,008 B2 * | 2/2021 | Shearer | A01B 79/005 |
| 2007/0068238 A1 | 3/2007 | Wendte | |
| 2012/0323452 A1* | 12/2012 | Green | A01B 79/005 701/50 |
| 2013/0046418 A1 | 2/2013 | Anderson | |
| 2017/0066325 A1 | 3/2017 | Brownell | |
| 2018/0232674 A1* | 8/2018 | Bilde | G06Q 10/06 |
| 2020/0113123 A1* | 4/2020 | Shearer | A01B 79/005 |
| 2020/0154626 A1* | 5/2020 | Schoeny | A01C 7/205 |
| 2020/0254829 A1 | 8/2020 | Schott et al. | |
| 2021/0008934 A1 | 1/2021 | Buhrke | |
| 2021/0173399 A1* | 6/2021 | Richard | B60W 50/14 |
| 2021/0276222 A1 | 9/2021 | Datema | |

(Continued)

FOREIGN PATENT DOCUMENTS

| | | |
|---|---|---|
| DE | 102009025494 A1 | 1/2011 |
| EP | 1493599 A2 | 1/2005 |
| EP | 3216628 A1 | 9/2017 |

(Continued)

OTHER PUBLICATIONS

U.S. Appl. No. 17/581,272 Office Action dated Dec. 18, 2023, 8 pages.

(Continued)

*Primary Examiner* — George C Jin
(74) *Attorney, Agent, or Firm* — Kelly, Holt & Christenson; Joseph R. Kelly

(57) ABSTRACT

A soil measure, such as a soil cone index, and a vehicle index indicating the amount of force the vehicle exerts on the ground as it travels over the ground, are obtained and compared to identify a soil damage score. The soil damage score can be mapped over a field and an agricultural vehicle can be controlled based upon the soil damage score.

20 Claims, 11 Drawing Sheets

(56) References Cited

U.S. PATENT DOCUMENTS

2021/0404812 A1\* 12/2021 Yuasa .................... A01B 37/00

FOREIGN PATENT DOCUMENTS

| EP | 2508057 B1 | 7/2018 |
| EP | 3415345 A1 | 12/2018 |
| EP | 2744322 B1 | 11/2019 |
| EP | 3763551 A1 | 1/2021 |
| WO | WO 03/023396 A2 | 3/2003 |
| WO | WO 2013/025890 A1 | 2/2013 |
| WO | WO 2013/112929 A2 | 8/2013 |

OTHER PUBLICATIONS

U.S. Appl. No. 17/581,297 Application and Drawings filed Jan. 21, 2022, 47 pages.
U.S. Appl. No. 17/715,407 Application and Drawings filed Apr. 7, 2022, 81 pages.
Extended European Search Report and Written Opinion issued in European Patent Application No. 23163772.9, daled Aug. 17, 2023, 7 pages.
Extended European Search Report and Written Opinion issued in European Patent Application No. 23152290.5, dated Jun. 22, 2023, in 8 pages.
Extended European Search Report and Written Opinion issued in European Patent Application No. 23152289.7, dated Jun. 21, 2023, in 7 pages.

\* cited by examiner

CONTROLLING AN AGRICULTURAL VEHICLE BASED ON SOIL DAMAGE SCORE

FIELD OF THE DESCRIPTION

The present description relates to agricultural machines. More specifically, the present description relates to agricultural vehicles that have a load that varies as the agricultural vehicle travels across a field.

BACKGROUND

There are a wide variety of different types of agricultural vehicles. Some such vehicles include sprayers, seeders and planters, air seeders, harvesters, nutrient spreaders, baling equipment, etc. All of these types of agricultural vehicles operate in a field and vary in weight over the course of the field.

The loads in these vehicles vary because the amount of material that is being gathered from the field (e.g., harvested), or applied to the field (e.g., sprayed), changes as the vehicle travels over the field. This can affect a number of things. For example, as the vehicle travels over the soil, it can inflict damage on the soil, such as undesired levels of compaction, among other things. Similarly, heavier vehicles may be more likely to become stuck in muddy areas or other areas within the field.

Some of these types of machines have a tire inflation system which can vary the inflation pressure in the tires of the vehicle. Other machines have a traction control system which can vary the torque applied to the ground engaging elements (e.g., wheels, tracks, etc.) different axels of the machine in order to increase traction.

In addition, the soil cone index is a measure of the strength of the soil, or a measure of the ability of the soil to carry a load. A cone penetrometer is a device which measures the force that it takes to push an element of the cone penetrometer tool into the soil. Thus, the cone penetrometer tool provides a soil cone index which indicates the ability of the soil to bear a load, and can also be an index indicative of the level of compaction of the soil.

The discussion above is merely provided for general background information and is not intended to be used as an aid in determining the scope of the claimed subject matter.

SUMMARY

A soil measure, such as a soil cone index, and a vehicle index indicating the amount of force the vehicle exerts on the ground as it travels over the ground, are obtained and compared to identify a soil damage score. The soil damage score can be mapped over a field and an agricultural vehicle can be controlled based upon the soil damage score.

Example 1 is a computer implemented method, comprising:
obtaining a soil measure for soil indicative of an ability of the soil to bear a load;
obtaining a vehicle index indicative of a force imparted by an agricultural vehicle on the soil, as a load corresponding to the agricultural vehicle varies as the agricultural vehicle travels over the field;
comparing the soil measure to the vehicle index to obtain a comparison result;
identifying a soil damage value based on the comparison result; and
generating a control signal to control the agricultural vehicle based on the soil damage value.

Example 2 is the computer implemented method of any or all previous examples wherein obtaining a soil measure comprises:
obtaining a plurality of different soil measure values, each soil measure value corresponding to a different geographic location across a field.

Example 3 is the computer implemented method of any or all previous examples wherein obtaining a vehicle index comprises:
identifying a plurality of different vehicle index values, each vehicle index value corresponding to a different geographic location across the field.

Example 4 is the computer implemented method of any or all previous examples wherein comparing the soil measure to the vehicle index comprises:
comparing each different soil measure value corresponding to a geographic location to a different vehicle index value corresponding to the geographic location.

Example 5 is the computer implemented method of any or all previous examples wherein identifying a plurality of vehicle index values comprises:
identifying the plurality of different vehicle index values accounting for the variation in the load as the agricultural vehicle travels along a travel path.

Example 6 is the computer implemented method of any or all previous examples wherein identifying the plurality of different vehicle index comprises:
identifying a set of vehicle characteristics corresponding to the agricultural vehicle; and
identifying the plurality of different vehicle index values accounting for the variation in the load as the agricultural vehicle travels along a travel path and based on the vehicle characteristics of the agricultural vehicle.

Example 7 is the computer implemented method of any or all previous examples wherein obtaining a plurality of different soil measure values comprises:
obtaining a map of each of the soil measure values mapped to the different corresponding geographic location.

Example 8 is the computer implemented method of any or all previous examples wherein obtaining a plurality of different soil measure values comprises:
obtaining, as the plurality of different soil measure values, a plurality of different cone index scores.

Example 9 is the computer implemented method of any or all previous examples wherein the agricultural vehicle is a planting machine and wherein obtaining a plurality of different soil measure values comprises:
detecting down force and down force margin on the planting machine; and
obtaining, as the plurality of different soil measure values, a plurality of proxy soil measure values based on the detected down force and down force margin.

Example 10 is the computer implemented method of any or all previous examples wherein obtaining a plurality of different soil measure values comprises:
obtaining a set of field characteristics corresponding to the field; and
predicting the plurality of different soil measure values based on the set of field characteristics.

Example 11 is the computer implemented method of any or all previous examples wherein obtaining a set of field characteristics comprises:

obtaining terrain data indicative of terrain along a travel path traveled by the agricultural vehicle across the field;

obtaining soil type data indicative of a soil type of the soil along the travel path; and obtaining soil moisture data indicative of soil moisture along the travel path.

Example 12 is an agricultural system, comprising:

at least one processor; and a data store that stores computer executable instructions which, when executed by the at least one processor cause the at least one processor to perform steps comprising:

obtaining a soil measure for soil indicative of an ability of the soil to bear a load;

obtaining a vehicle index indicative of a force imparted by an agricultural vehicle on the soil, as a load corresponding to the agricultural vehicle varies as the agricultural vehicle travels over the field;

comparing the soil measure to the vehicle index to obtain a comparison result;

identifying a soil damage value based on the comparison result; and generating a control signal to control the agricultural vehicle based on the soil damage value.

Example 13 is the agricultural system of any or all previous examples wherein obtaining a soil measure comprises:

obtaining a plurality of different soil measure values, each soil measure value corresponding to a different geographic location across a field.

Example 14 is the agricultural system of any or all previous examples wherein obtaining a vehicle index comprises:

identifying a plurality of different vehicle index values, each vehicle index value corresponding to a different geographic location across the field.

Example 15 is the agricultural system of any or all previous examples wherein comparing the soil measure to the vehicle index comprises:

comparing each different soil measure value corresponding to a geographic location to a different vehicle index value corresponding to the geographic location.

Example 16 is the agricultural system of any or all previous examples wherein identifying a plurality of vehicle index values comprises:

identifying the plurality of different vehicle index values accounting for the variation in the load as the agricultural vehicle travels along a travel path.

Example 17 is the agricultural system of any or all previous examples wherein obtaining a plurality of different soil measure values comprises:

obtaining a map of each of the soil measure values mapped to the different corresponding geographic location.

Example 18 is the agricultural system of any or all previous examples wherein obtaining a plurality of different soil measure values comprises:

obtaining a set of field characteristics corresponding to the field; and predicting the plurality of different soil measure values based on the set of field characteristics.

Example 19 is a computing system, comprising:

a soil measure identification system obtaining a soil measure for soil indicative of an ability of the soil to bear a load;

a vehicle index identification system obtaining a vehicle index indicative of a force imparted by an agricultural vehicle on the soil, as a load corresponding to the agricultural vehicle varies as the agricultural vehicle travels over the field;

a soil damage score generation system configured to compare the soil measure to the vehicle index to obtain a comparison result and identify a soil damage value based on the comparison result; and a control signal generator generating a control signal to control the agricultural vehicle based on the soil damage value.

Example 20 is the computing system of any or all previous examples wherein the soil measure identification system is configured to obtain a plurality of different soil measure values, each soil measure value corresponding to a different geographic location across a field, wherein the vehicle index identification system is configured to identify a plurality of different vehicle index values, each vehicle index value corresponding to a different geographic location across the field, and wherein the soil damage score generation system is configured to compare each different soil measure value corresponding to a geographic location to a different vehicle index value corresponding to the geographic location.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

Figure 1:
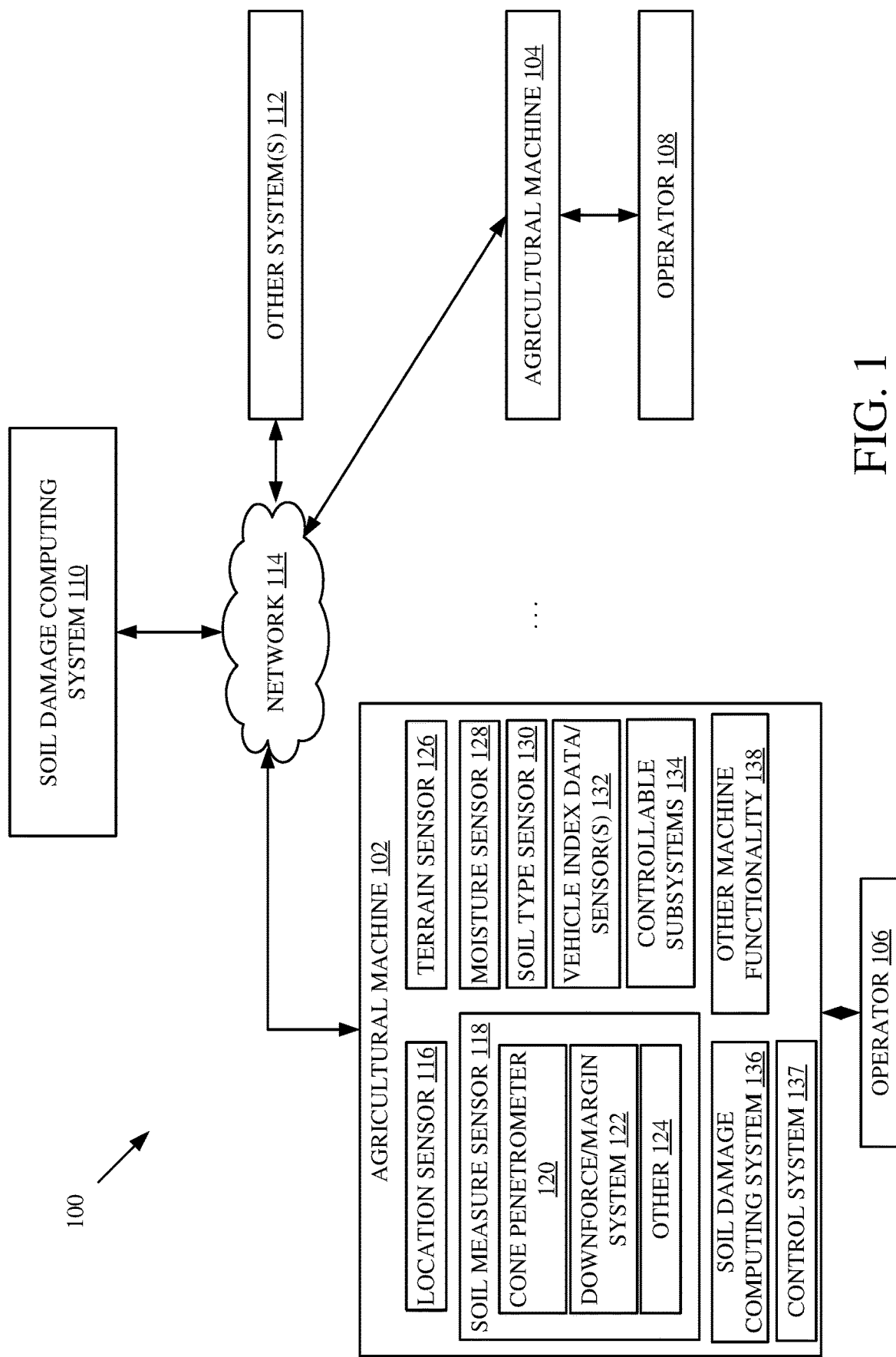
FIG. 1 is a block diagram of one example of an agricultural system.

FIG. 1 is a block diagram of one example of an agricultural system 100. Agricultural system 100 includes a set of agricultural machines 102-104 that are operated by operators 106-108, respectively. In the example shown in FIG. 1, a soil damage computing system 110 is shown communicating with agricultural machines 102-104, and other systems 112, over network 114. It will be noted that soil damage computing system 110 can be deployed on one or more of the agricultural machines 102-104 or on other systems 112 as well, but it is shown as a separate system that is accessed over network 114 by agricultural machines 102-104. System 110 can be distributed among various machines and locations as well.

Network 114 can be a local area network, a wide area network, a cellular communication network, a near field communication, or any of a wide variety of other networks or combinations of networks. The other systems 112 can be farm managers systems, vendor systems, manufacture systems, or any of a wide variety of other computing systems.

Agricultural machine 102 illustratively includes location sensor 116, soil measure sensor 118 (which can include cone potentiometer 120, downforce/margin system 122 and other items 124), terrain sensor 126, moisture sensor 128, soil type sensor 130, vehicle index data/sensors 132, controllable subsystems 134, soil damage computing system 136, control system 137, and other agricultural machine functionality 138. Agricultural machines 102-104 can be any of a wide variety of different types of agricultural machines. In some examples, machines 102-104 are machines that vary in weight as they travel over an agricultural field performing an agricultural operation. Such agricultural machines or vehicles can be agricultural machines, such as planting machines (which vary in weight based on seeding rate), material application systems (such as a sprayer which varies in weight as it applies material to a field), a harvester (which varies in weight at it harvests material in the field), and any of a wide variety of other machines. Location sensor 116 can be a global navigation satellite system (GNSS) receiver or another location sensor that senses the geographic location of agricultural machine 102. Such sensors can also include a dead reckoning system, or any of a wide variety of other sensors.

Terrain sensor 126 can sense the type of terrain (such as the terrain elevation, slope, etc.). Sensors 126 can be a gyroscopic sensor, an accelerometer, or any of a wide variety of other inertial measurement units, or terrain sensors that can sense the orientation of agricultural machine 102 as it travels through the field.

Moisture sensor 128 illustratively senses the moisture of the soil. Moisture sensor 128 can be a sensor probe mounted to machine 102 to engage the soil, or another sensor 128. Soil type sensor 130 is illustratively a sensor that senses the type of soil over which machine 102 is traveling. In one example, soil samples are taken and analyzed and then geographically correlated to the field. In other examples, soil type sensor 130 can be a sensor disposed on a different machine that samples and senses the soil type during a prior operation. Other soil type sensors can be used as well.

Soil measure sensor 118 generates a measure indicative of the ability of the soil to support a load. In one example, sensor 118 can be a cone penetrometer 120. Cone penetrometer 120 can be a mechanism that penetrates the soil during the operation of machine 102 and generates an output indicative of a cone index value. The cone index value for the soil is a measure of the resistance to penetration of the soil. Downforce/margin system 122 generates a proxy indicative of the cone index or otherwise indicative of the ability of the soil to bare a load. For instance, the downforce/margin system 122 can measure the downforce exerted by a row unit of a planter and reduce the measured downforce by the downforce margin which is the load borne by the gauge wheels of a row unit. This is indicative of the overall resistance imparted on the soil by the row unit and may be a proxy indicative of the cone index or otherwise indicative of the ability of the soil to bear a load.

Vehicle index data/sensors 132 sense a variable or other item that can be used to calculate a vehicle index indicative of the amount of force (e.g., in pounds per square inch or in other units) that machine 102 will exert on the soil as it travels over the soil. The vehicle index data/sensors 132 can be pre-stored data indicative of the weight of the machine, and indicative of how the weight of the machine will vary over its full-to-empty, or empty-to-full cycle. In another example, the data/sensors 132 can be sensors that sense the actual weight of the vehicle (such as load sensors in the axels of the vehicle, etc.) or another variable that is indicative of the force that the vehicle will impart to the ground as it travels over the field.

Controllable subsystems 134 on machine 102 can include such things as a vehicle navigation subsystem, a tire inflation subsystem, a load re-distribution subsystem, an operator interface subsystem, a traction control subsystem, a communication subsystem, a machine setting subsystem, among others. Soil damage computing system 136 can obtain the soil measure generated by soil measure sensor 118 indicative of the soils ability to support a load, and the vehicle index generated by vehicle index data/sensors 132 indicative of the force or load that machine 102 will apply to the soil. Based upon these values, soil damage computing system 136 can compute a soil damage metric indicative of a compaction of the soil, or other item of soil damage that will be imparted, or is being imparted, by machine 102 as machine 102 is traveling over the field.

It will be noted that soil damage computing system 136 need not necessarily reside on agricultural machine 102, but can be separate from machine 102 (as indicated by soil damage computing system 110) and accessed over network 114. In one example, soil damage computing system 136 or 110 can generate a near real time soil damage metric indicative of the soil damage (if any) being imparted by machine 102 on the soil over which it is traveling. In another example, the soil damage computing system 136, 110 can generate a predictive value indicative of the predicted soil damage that machine 102 will impart on the soil if it travels over the soil in the future.

Based on the soil damage metric, control system 137 can generate control signals to control the controllable subsystems 134. For instance, where the soil damage metrics indicate a relatively large degree of soil damage (compared to a threshold value input by the user or a default threshold or another threshold), control system 137 can generate control signals to control the tire inflation subsystem to deflate the tires to increase the contact patch between the tire and the ground, and thus to spread the force imparted by machine 102 on the soil over a large area. In another example, control system 137 can generate control signals to output a display or other operator output that can be used to notify the operator of the level of damage that is being, or will be, imparted on the soil. In yet another example, control system 137 can control a navigation system to engage a path planning system to generate a recommended path through the field that will reduce the overall damage to the soil. For instance, the path planning system may generate a path that has machine 102 traveling over particularly susceptible spots in the field (such as low spots, muddy spots, etc.) when machine 102 is closer to empty than full so that machine 102 is imparting less force on the field. In another example, the path planning system may plan a path that avoids the vulnerable areas until later in the day (such as when they dry out), etc. These are just examples and other examples are contemplated herein as well. In yet another example, control system 137 can communicate the soil damage metric to other agricultural machines 104, to other systems 112, etc.

Figure 2:
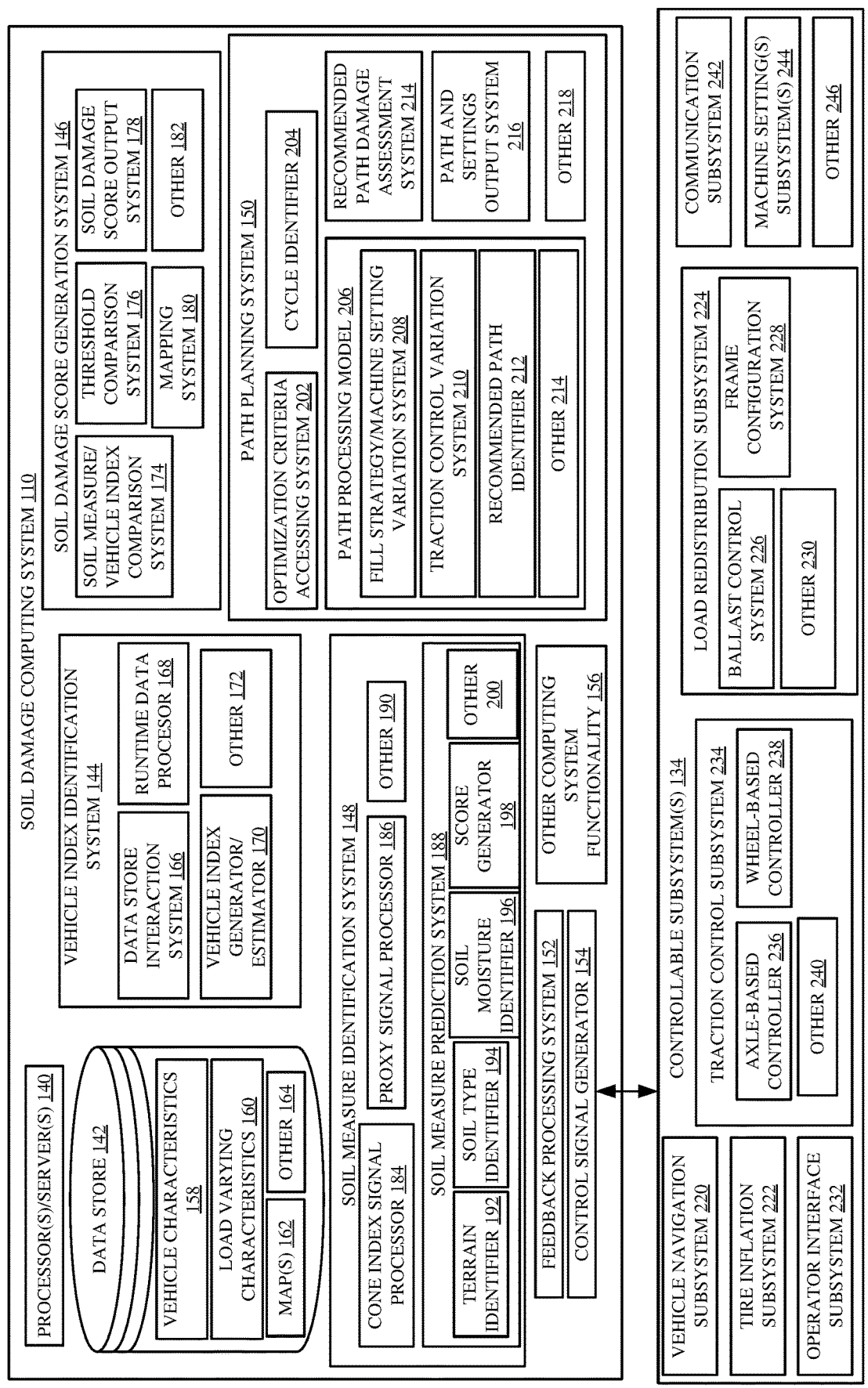
FIG. 2 is a block diagram showing one example of a soil damage computing system.

FIG. 2 is a block diagram showing one example of the soil damage computing system in more detail. For purposes of the present discussion, it will be assumed that soil damage computing system 110 is being shown and described in FIG. 2. Also, soil damage computing systems 110 and 136 can be similar or different. For purposes of the present description it will be assumed that they are similar so that only soil damage computing system 110 is described in more detail.

FIG. 2 shows that, in one example, soil damage computing system 110 can include one or more processors or servers 140, data store 142, vehicle index identification system 144, soil damage score generator system 146, soil measure identification system 148, path planning system 150, feedback processing system 152, control signal generator 154, and other computing system functionality 156. Data store 142 can store vehicle characteristics 158, load varying characteristics 160, maps 162, and other items 164. Vehicle index identification system 144 can include data store interaction system 166, runtime data processor 168, vehicle index generator/estimator 170, and other items 172. Soil damage score generation system 146 can include soil measure/vehicle index comparison system 174, threshold comparison system 176, soil damage score output system 178, mapping system 180, and other items 182.

Soil measure identification system 148 can include cone index signal processor 184, proxy signal processor 186, soil measure prediction system 188, and other items 190. Soil measure prediction system 188 can include terrain identifier 192, soil type identifier 194, soil measure identifier 196, score generator 198, and other items 200. Path planning system 150 can include optimization criteria accessing system 202, cycle identifier 204, and path processing model 206 (which can include fill strategy/machine setting variation system 208, traction control variation system 210, recommended path identifier 212, and other items 214). Path planning system 150 can include recommended path damage assessment system 214, suggested path and settings output system 216, and other items 218.

FIG. 2 also shows that controllable subsystems 134 can include vehicle navigation subsystem 220, tire inflation subsystem 222, load redistribution subsystem 224 (which can include ballast control system 226, frame configuration system 228, and other items 230), operator interface subsystem 232, traction control subsystem 234 (which can include axel-based controller 236, wheel-based controller 238 and other items 240), communication subsystem 242, machine settings subsystem 244, and other items 246. Before describing soil damage computing system 110, and its operation, in more detail, a description of some of the items in soil damage computing system 110, and their operation, will first be provided.

Vehicle characteristics 158 can include the physical dimensions of the vehicle, the weight of the vehicle, the model and make of the vehicle, among other things. Load varying characteristics 160 can be data indicative of how the load carried by the vehicle varies throughout its full-to-empty or empty-to-full cycle. For instance, load varying characteristics may include a lookup table, a curve, or other model or data that indicate how quickly the load of a seeding machine drops as it is seeding at a particular seed population rate, at a particular ground speed, etc. The load varying characteristics 160, in another example, indicate how the load of a harvester increases as it is harvesting a particular hybrid, with a moisture level, in a field that has a particular estimated yield, at a particular harvester speed, etc. These are examples only and a wide variety of other models, data structures, or mechanisms can be used to indicate that load varying characteristics 160 of a vehicle. Maps 162 may include terrain maps, soil type maps, yield maps, soil measure maps, soil damage maps, moisture maps, vehicle index maps, or other maps that indicate characteristics of the field, characteristics of the machine as those characteristics vary over the field, or other information.

Vehicle index identification system 144 generates the vehicle index which indicates the amount of force that the vehicle or machine 102 will exert on the soil over which it is traveling. Data store interaction system 166 can interact with data store 142 to obtain the vehicle characteristics 158 and/or the load varying characteristics 160 and/or maps 162. Runtime data processor 168 can obtain runtime information from vehicle index data/sensors 132 that may be used to derive the vehicle index value for machine 102. Vehicle index generator/estimator 170 can then either generate the vehicle index value, or estimate that value, based upon the information obtained. For instance, when runtime data processor 168 is generating data indicative of how the load of the vehicle is changing over time, vehicle index generator 170 can use that information in conjunction with the vehicle characteristics 158 and/or other information to generate a vehicle index value indicative of the actual load being imparted on the soil by the agricultural machine. When the information is indicative of how the load of the vehicle will change in the future during its empty-to-full or full-to-empty cycle, then vehicle index generator/estimator 170 can estimate the vehicle index value at a time in the future, or at a location in the field, etc.

Soil measure identification system 148 generates a soil measure value indicative of the ability of the soil to bear a load. Cone index signal processor 184 can receive the signal from cone penetrometer 120 and process that signal to obtain a cone index value indicative of the cone index value for the soil sensed by cone index penetrometer 120. Proxy signal processor 186 can receive the signal from a proxy of the cone index (e.g., from downforce/margin system 122) and process that signal to identify the soil measure value from the proxy signal.

Soil measure prediction system 188 can generate a prediction of the soil measure at different points over the field, based upon the information generated by a plurality of different sensors, or generated in other ways. For instance, terrain identifier 192 can identify the type of terrain 1 in the field based on a signal from terrain sensor 126 (shown in FIG. 1) or may obtain the terrain information from maps 162 or in other ways. Soil type identifier 194 can obtain a soil type at different locations in the field from a soil type sensor 130 or from soil maps 162 or in other ways. Soil moisture identifier 196 can obtain the soil moisture values for soil at different locations in the field from moisture sensor 128 or from soil moisture maps 162 or in other ways. For instance, based upon the terrain, soil moisture identifier 196 may identify low spots. Based on weather information, such as precipitation information, sun information, temperature information, wind information, etc. soil moisture identifier 196 can estimate soil moisture at different locations in the field. Score generator 198 can generate the soil measure value indicative of the ability of the soil to bear a load based upon the information from identifiers 192, 194, 196, and/or other information generated by other items 200.

Soil damage score generation system 146 obtains the vehicle index from vehicle index identification system 144 and the soil measure from soil measure identification system 148 and generates a soil damage score which can be used by path planning system 150 and/or control signal generator 154 to generate control signals for controlling controllable subsystem 134.

Soil measure/vehicle index comparison system illustratively converts the soil measure and the vehicle index to comparable units (such as pounds per square inch, etc.) and compares the soil measure to the vehicle index to determine whether the vehicle will damage the soil. For instance, if the vehicle index exceeds the soil measure, this means that the force that the vehicle will exert on the soil exceeds the ability of the soil to bear a load, and thus will result in compaction. However, some compaction may be acceptable. Therefore, threshold comparison system 176 determines whether the amount by which the vehicle index exceeds the soil measure meets a threshold level. The threshold level may indicate when undesirable soil damage occurs. The threshold level may be input by the operator, it may be empirically determined, it may be a default or dynamically changing value, among other things.

Mapping system 180 can generate a map of the soil damage scores. The map may be of scores from actual sensed values, or a predictive map that predicts the soil damage scores based upon the load variation of the agricultural machine as it travels over the field (and thus based on its varying vehicle index values) and based upon the predicted soil measures of the soil in the field generated by soil measure prediction system 188. The soil damage scores can be stored in maps or in other ways as well and soil damage score output system 178 can generate an output indicative of the soil damage scores. For instance, soil damage score output system 178 may provide an output to path planning system 150 and/or control signal generator 154. Soil damage score output system 178 can provide an output to other computing system functionality 156 as well.

Path planning system 150 can receive the output from soil damage score output system 178 and perform path planning to identify paths that the machine should take through the field when performing its operation. In another example, path planning system 150 may generate a timing or scheduling output indicative of when the machine should perform its path or other outputs as well.

Optimization criteria accessing system 202 identifies the optimization criteria that are to be used in path planning. For instance, the optimization criteria may be stored in data store 142 or elsewhere. The optimization criteria may be input by the operator, or they may be default criteria. The optimization criteria may be dynamically changed or set in other ways. By way of example, it may be that the path planning system is to calculate a path for the agricultural machine through the field optimizing productivity. In another example, the path may be calculated optimizing the soil damage score (to reduce soil damage wherever possible). The optimization criteria may be to plan the agricultural operation to take place as quickly as possible, thus optimizing speed. The optimization criteria accessing system 202 may access optimization criteria in other ways, and those criteria may be other criteria as well.

Cycle identifier 204 identifies the full-to-empty cycle of the agricultural machine (or the empty-to-full cycle where appropriate). Identifier 204 may identify the distance that the machine can travel during the cycle, the time the machine will take to travel over that cycle, or other characteristics or parameters of the full-to-empty cycle or the empty-to-full cycle of the agricultural machine. Once the optimization criteria are known, and the cycle of the agricultural machine is known, then path processing model 206 performs path processing to identify a recommended path through the field for the agricultural machine.

Path processing model 206 can be any type of model that generates a path output to optimize the optimization criteria. In generating the path, model 206 varies different variables, such as the geographic location of the path, the traction control that is used, the fill strategy and machine settings that are used by the machine (such as how full the machine is filled and when it is unloaded during different paths, etc.), among other things. By way of example, fill strategies/machine settings variation system 208 varies the fill strategies and machine settings so that path processing model 206 can model paths, optimizing on the optimization criteria, with different fill strategies in different machine settings. Traction control variation system 210 varies the traction control strategies or settings that are used to control traction on the machine so that model 206 can model different paths through the field, optimizing based upon the optimization criteria, using different traction control settings or traction control strategies. Other items can be varied so that model 206 can model different paths through the field with other variations as well. Recommended path identifier 212 identifies the recommended path, with a recommended fill strategy and set of machine settings, as well as traction control variations that were modeled.

Recommended path damage assessment system 214 then analyzes the recommended path to access the soil damage that will be created by the machine, if it follows the recommended path. For instance, it may be that path processing model 206 outputs the recommended path, but even the recommended path may cause an undesirable amount of damage. Therefore, system 214 assesses the soil damage that will be inflicted by the machine, and can generate an output indicative of the damage. Recommended path and settings output system 216 then generates an output indicative of the recommended path and the recommended settings (e.g., fill strategy, machine settings, traction control strategy and settings, etc.).

System 216 can also output an indication of the damage that will be inflicted, as determined by recommended path damage assessment system 214. System 216 may output the recommended path as a navigational path indicating the geographic path that the machine is to take in order to follow the recommended path. The recommended path can be output to a navigation system which can automatically navigate the machine along the path, or it can be output to an operator so that the operator can manually navigate the machine over that path, or it can be output in other ways. Similarly, the recommended settings can be output so that they can be automatically set on the machine or set by an operator, etc.

Control signal generator 154 can receive the recommended path and settings output by system 216 and generate control signals to control controllable subsystems 134 based upon the recommended path and settings. For instance, control signal generator 154 can generate output signals to control vehicle navigation subsystem 280 to automatically navigate the agricultural machine through the recommended path. Where the settings include tire inflation settings, then control signal generator 154 can generate control signals to control tire inflation subsystem 222 to automatically inflate and deflate the tires, as the agricultural machine travels along the recommended path, based upon the tire inflation settings.

It may also be that the recommended settings are settings for a load redistribution subsystem 224 that can be used to redistribute the load on the agricultural machine about its frame. Therefore, control signal generator 154 can generate control signals to accomplish the desired load redistribution using subsystem 224. By way of example, it may be that the agricultural vehicle is configured with a ballast control signal system 226 that can mechanically move ballast about the agricultural machine to change where the load imparted by the machine is imparted to the soil over which it is traveling. Control signal generator 154 can generate control signals to control ballast control system 226 to redistribute the ballast on the machine based upon the recommended settings. Frame configuration system 228 can be controlled to reconfigure the frame of the agricultural machine, such as to collapse the machine, expand the machine, etc., to change the way the load from the machine is imparted to the field over which it is traveling. The frame configuration system 228 can use hydraulic or pneumatic cylinders or other electrical, mechanical, pneumatic, hydraulic, or other actuators to change the configuration of the machine frame. The control signals generated by control signal generator 154 can be used to control those actuators to move the frame to a desired configuration.

Traction control system 234 can use axel-based controllers 236 to control the torque applied by individual axels on the agricultural machine. Wheel-based controller 238 can be used to control the torque applied by individual wheels or individual tracks or other individual ground engaging mechanisms. Therefore, control signal generator 154 can generate control signals to control the axel-based controller 236 and/or the wheel-based controller 238 to perform traction control on the agricultural vehicle based upon the recommended settings.

Operator interface subsystem 232 can include any operator interface subsystems that the operator 106 can use to control agricultural machine 102, such as a steering wheel, joysticks, levers, linkages, pedals, buttons, a touch sensitive display screen or another display screen, a microphone and speaker (where speech synthesis and speech recognition are used), or a wide variety of other audio, visual, and haptic user interface elements. Operator interface subsystem 232 can thus display or otherwise communicate the recommended path and settings to the operator and thus control signal generator 154 can generate control signals to control operator interface subsystem 232 to perform that type of communication with the operator.

Communication subsystem 242 can be controlled to communicate the recommended path and settings to other systems 112, other agricultural machines 104, etc. Machines setting subsystem 246 can be used to automatically set the machine settings to the suggested settings. Therefore, control signal generator 154 can generate control signals to control machine settings subsystem 244 to set the machine settings to the recommended settings.

Figure 3:
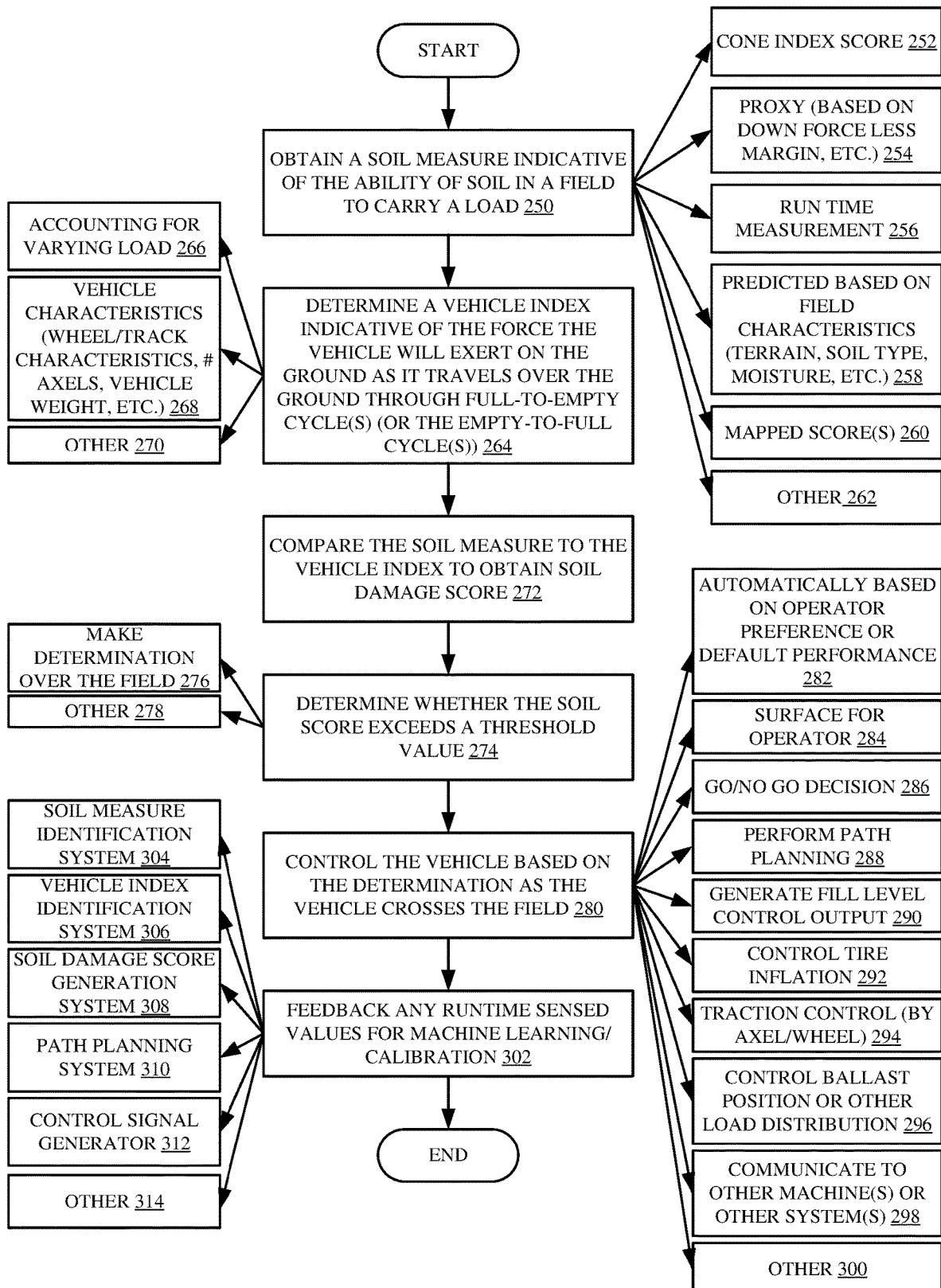
FIG. 3 is a flow diagram illustrating one example of the overall operation of an agricultural system.

FIG. 3 is a flow diagram illustrating one example of the overall operation of the agricultural system 100, in controlling agricultural machine 102 based upon a soil damage score that is calculated by soil damage score generation system 146. Soil damage score generation system 146 obtains a soil measure indicative of the ability of the soil in a field to carry a load from soil measure identification system 148. Obtaining the soil measure is indicated by block 250 in the flow diagram of FIG. 3. The soil measure can be a cone index score 252, a proxy 254, such as a signal based on the downforce, less the downforce margin, etc. The soil measure can be based on a runtime measurement taken (such as from a cone penetrometer 120, as indicated by block 256) or the soil measure can be a predicted value based upon field characteristics, such as the terrain, soil type, moisture, etc., as indicated by block 258. The soil measure may be a map of soil measure scores through the field, as indicated by block 260, or it can be provided in a wide variety of other ways, as indicated by block 262.

Soil damage score generation system 146 then determines a vehicle index. The vehicle index can account for the variation in the load based upon the load varying characteristics 160 in data store 142, or in other ways. For instance, system 146 can obtain the vehicle index from vehicle index identification system 144. The vehicle index is indicative of the force that the vehicle will exert on the ground as the vehicle travels over the ground through the full-to-empty cycle or the empty-to-full cycle, as indicated by block 264 in the flow diagram of FIG. 3. The vehicle index identification system 144 can generate the vehicle index accounting for the varying load that the vehicle will carry as it travels over the field, as indicated by block 266. The vehicle index can take into account the vehicle characteristics 158, as indicated by block 268, and other items as indicated by block 270. Soil measure/vehicle index comparison system 174 then compares the soil measure to the vehicle index to obtain a soil damage score, as indicated by block 272. Threshold comparison system 176 determines whether the soil damage score exceeds a threshold value, as indicated by block 274. Mapping system 180 can generate the soil damage score over the entire field, as indicated by block 276, and the soil damage score can be compared against a threshold in other ways as well, as indicated by block 278.

Control signal generator 154 can then generate control signals to control subsystems 134 of the agricultural machine, as it crosses the field. Controlling the vehicle is indicated by block 280 in the flow diagram of FIG. 3. The vehicle can be controlled automatically or based on operator preference or default values, as indicated by block 282. The soil damage scores can be surfaced for the operator, as indicated by block 284, and control signal generator 154 can make a go/no go decision and surface that for the operator through operator interface subsystem 282, as indicated by block 286. For instance, control signal generator 154 may determine that the damage scores are so high that the machine should not perform the agricultural operation until a later time when the soil stabilizes, or firms up, or under other circumstances. This can be displayed for the user, or otherwise surfaced for the user, through an operator interface subsystem 232.

Path planning system 150 can perform path planning based on the damage scores, as indicated by block 288. The path processing model 206 can generate a recommended fill strategy, as indicated by block 290, and that recommended fill strategy can be output to the operator or to the machine for automatic control as well.

Tire inflation subsystem 222 can be controlled to control the tire inflation based upon the soil damage scores, as indicated by block 292. Traction control system 234 can be controlled to control the traction control on an individual axel basis or on an individual wheel basis, as indicated by block 294. Load redistribution subsystem 224 can be controlled to control the ballast position or other load distribution, as indicated by block 296. Communication subsystem 242 can be used to communicate the recommended path, the soil damage scores, the recommended machine settings, etc., to other machines or other systems, as indicated by block 298. The machine can be controlled in a wide variety of other ways as well, as indicated by block 300.

It should also be noted that, in one example, the values that have been estimated or predicted by soil damage computing system 110 can be modified by feedback processing system 152 which may obtain actual, measured values and perform machine learning on the various functionality in soil damage computing system 110 that generates estimates or predictions to improve the accuracy of those estimates or predictions. Similarly, estimated or predicted values can be modified or calibrated by feedback processing system 152 based upon actual measured values as well. Feeding back any runtime sensed values for machine learning and/or calibration is indicated by block 302 in the flow diagram of FIG. 3. For instance, where soil measure prediction system 188 predicts a cone index value or other soil measure, then a measured cone index value may be fed back, for processing by feedback processing 152 so that the algorithm used by soil measure prediction system 188 can be trained using machine learning or other techniques for more accuracy. Also, other predicted values can be modified or calibrated to improve their accuracy based on the actual, measured value(s). Performing feedback to the soil measure identification system is indicated by block 304 in the flow diagram of FIG. 3.

Also, in an example in which vehicle index generator/estimator 170 generates an estimated value for the vehicle, a vehicle index sensor 132 may sense the actual vehicle index value (such as the weight of the vehicle, etc.). The actual sensed value may be fed back to feedback processing system 152 for processing using machine learning or other algorithms to improve the estimation generated by vehicle index generator/estimator 170. Estimated values can be calibrated based on the fed back values as well. Feeding the information back for improving the accuracy of vehicle index identification system 144 is indicated by block 306 in the flow diagram of FIG. 3.

These or other measured values may also be fed back to soil damage score generation system 146 to improve the accuracy of that system, as indicated by block 308. Measured values can also be fed back to path planning system 150 to improve the path planning as indicated by block 310. For instance, where path planning system 150 generates a recommended path and recommended settings, those settings and the characteristics of the path can be sensed and fed back to path planning system 150 for machine learning to improve path planning and recommended settings. The measured values can be processed by feedback processing system 152 to improve the control signals generated by control signal generator 154 as well, as indicated by block 312. Measured values can be fed back in other ways, for use by other machine learning or calibration algorithms as well, as indicated by block 314.

Figure 4:
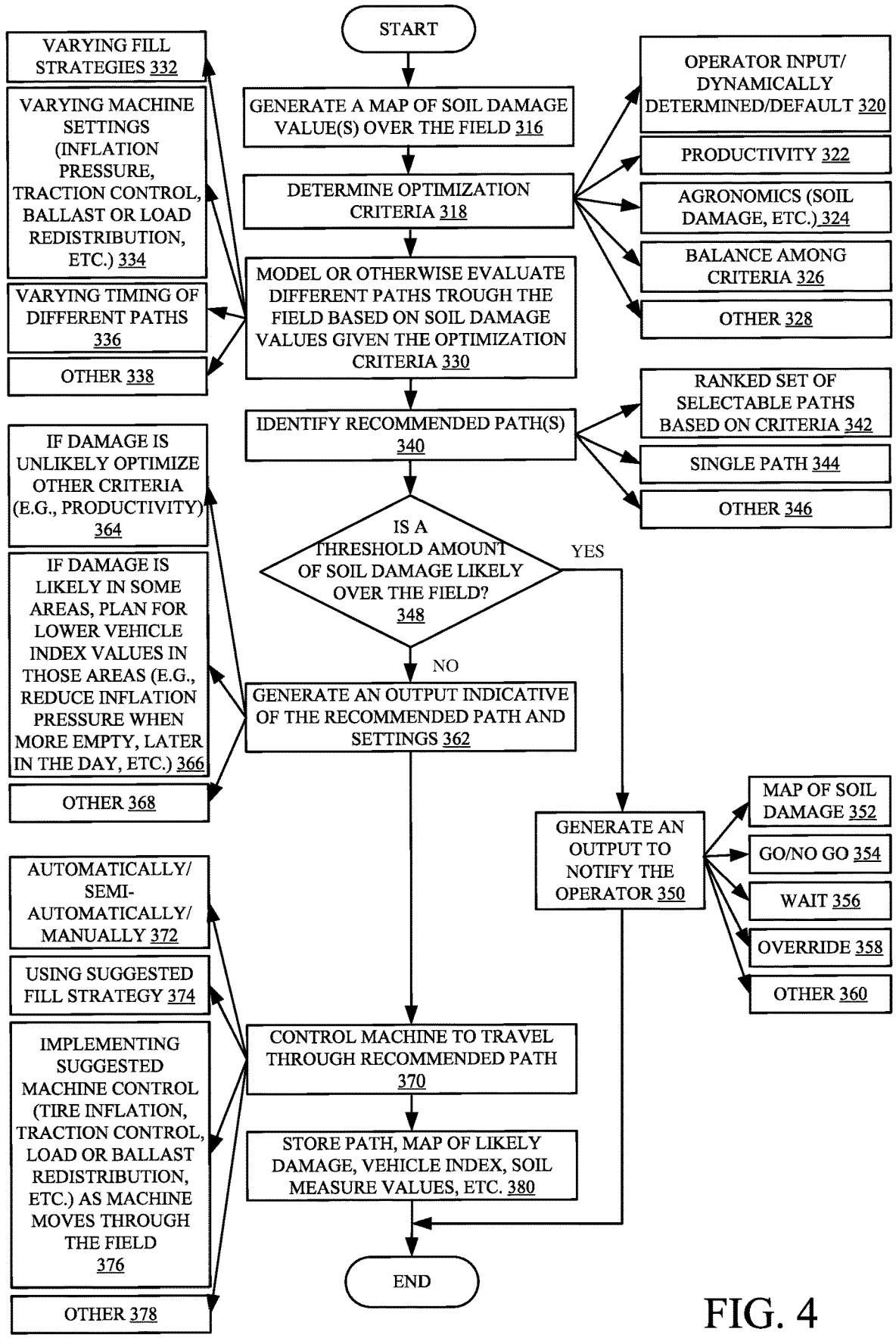
FIG. 4 is a flow diagram illustrating one example of the operation of a path planning system in generating a path plan based upon a soil damage score.

FIG. 4 is a flow diagram illustrating one example of the operation of path planning system 150, in more detail. It is first assumed that soil damage score generator system 146 uses mapping system 180 to generate a map of soil damage values over the field upon which the machine will be performing in agricultural operation. Generating a map of the soil damage values over the field is indicated by block 316 in the flow diagram of FIG. 4. Optimization criteria accessing system 202 then determines the optimization criteria that are to be used by path planning system 150 in identifying a recommended path. Determining the optimization criteria is indicated by block 318 in the flow diagram of FIG. 4. The optimization criteria may be determined based on an operator input, the optimization criteria may be determined dynamically, or the optimization criteria may be default values that are obtained from data store 142, as indicated by block 320. The optimization criteria may be productivity 322, or agronomics (such as soil damage) 324.

The optimization criteria may call for a balance between productivity and agronomics, as indicated by block 326. The optimization criteria may be other criteria and they may be obtained in other ways as well, as indicated by block 328.

Path processing model 206 then models or otherwise evaluates different paths through the field based on the soil damage values given the optimization criteria, as indicated by block 330. The different paths may be evaluated by varying the fill strategies as indicated by block 332 and by varying the machine settings (such as tire inflation pressure, traction control, ballast or load redistribution, etc.), as indicated by block 334. The various paths through the field can be evaluated based on the optimization criteria by varying the timing when the agricultural machine will be at different points in the field, as indicated by block 336. The different paths can be modeled or evaluated by varying a wide variety of other parameters, and in a wide variety of other ways, as indicated by block 338.

Recommended path identifier 212 then identifies on or more recommended paths, as indicated by block 340. In one example, recommended path identifier 212 identifies a plurality of different recommended paths that are ranked based on the optimization criteria, and are output as different selectable paths. Outputting the ranked paths as different selectable paths based on the optimization criteria is indicated by block 342. Recommended path identifier 212 may output the recommended path as a single path, as indicated by block 344, or in other ways, as indicated by block 346.

Recommended path damage assessment system 214 then determines whether a threshold amount of soil damage is likely over the field if the vehicle follows the recommended path. Again, the threshold can be input by the operator, it can be a default threshold, or it can be a dynamically determined threshold or another threshold. Determining whether a threshold amount of soil damage is likely over the field is indicated by block 348 in the flow diagram of FIG. 4.

If so, then an indication that the threshold amount of soil damage is likely to occur is output to control signal generator 154 which generates an output on operator interface subsystem 232 notifying the operator that a threshold amount of damage will occur over the field, as indicated by block 350. The output may be a map of the likely soil damage, as indicated by block 352, or the output can be a simple go/no go indicator indicating that the agricultural operation should not be performed at this time, as indicated by block 354. The output may be an indication that the operation should be delayed for a certain amount of time, as indicated by block 356. The output may include an override actuator so that the operator can override the output, as indicated by block 358, and then continue to perform the agricultural operation. The output notifying the operator can be any of a wide variety of other outputs notifying the operator in other ways as well, as indicated by block 360.

Assuming that a threshold amount of soil damage is not likely to occur over the field when navigating through the recommended path, then the recommended path and settings output system 216 generates an output indicative of the recommended path and recommended settings, as indicated by block 362. In one example, if damage is unlikely, then the recommended path is optimized based on criteria other than damage, such as productivity, as indicated by block 364. If the damage is likely in some sensitive areas, then the recommended path is illustratively a path which plans to have the agricultural vehicle traveling over those sensitive areas when it has a lower vehicle index. This may include reducing the tire inflation pressure over those areas, it may include driving the vehicle over those areas when the vehicle is less full than at other times, or it may include having the vehicle travel over those areas later in the day so that the areas have a chance to dry out, and firm up, etc., as indicated by block 366. The output of the recommended path and settings may be generated in other ways as well, as indicated by block 368. Control signal generator 154 receives the recommended path and settings output by system 216 and generates control signals to control controllable subsystems 134 so that the agricultural machine travels through the recommended path, as indicated by block 370. In one example, the control signals can be applied to vehicle navigation system 220 to automatically control the vehicle to travel through the recommended path. In another example, the control signals can control the vehicle navigation subsystem 220 to travel through the recommended path semiautomatically (such as controlling the vehicle automatically during a pass through the field and controlling the vehicle manually during turns), or the control signal generator 154 can generate control signals to control operator interface subsystem 232 so that the operator can manually control the agricultural vehicle to travel over the recommended path. Controlling the agricultural vehicle to travel automatically, semiautomatically, or manually over the recommended path is indicated by block 372 in the flow diagram of FIG. 4.

The control signal generator 154 can control controllable subsystems 134 to implement a suggested fill strategy (such as to fill the machine partially full, to unload the machine with material to be applied after the machine is only partially full during harvesting, or to employ other fill strategies), as indicated by block 374. Similarly, control signal generator 154 can generate control signals to control the controllable subsystems 134 to implement other desired machine control, such as to control tire inflation pressure, traction control, load or ballast redistribution, etc., as the agricultural machine moves through the field over the recommended path, as indicated by block 376. The control signal generator 154 can generate control signals in other ways to perform other control operations as well, as indicated by block 378.

In one example, soil damage computing system 110 then stores the recommended path, the map of the likely soil damage values, the vehicle index and soil measure values, and any other desired values or information corresponding to the recommended path, as indicated by block 380. The information can be stored in data store 142 or in other systems.

Figure 5:
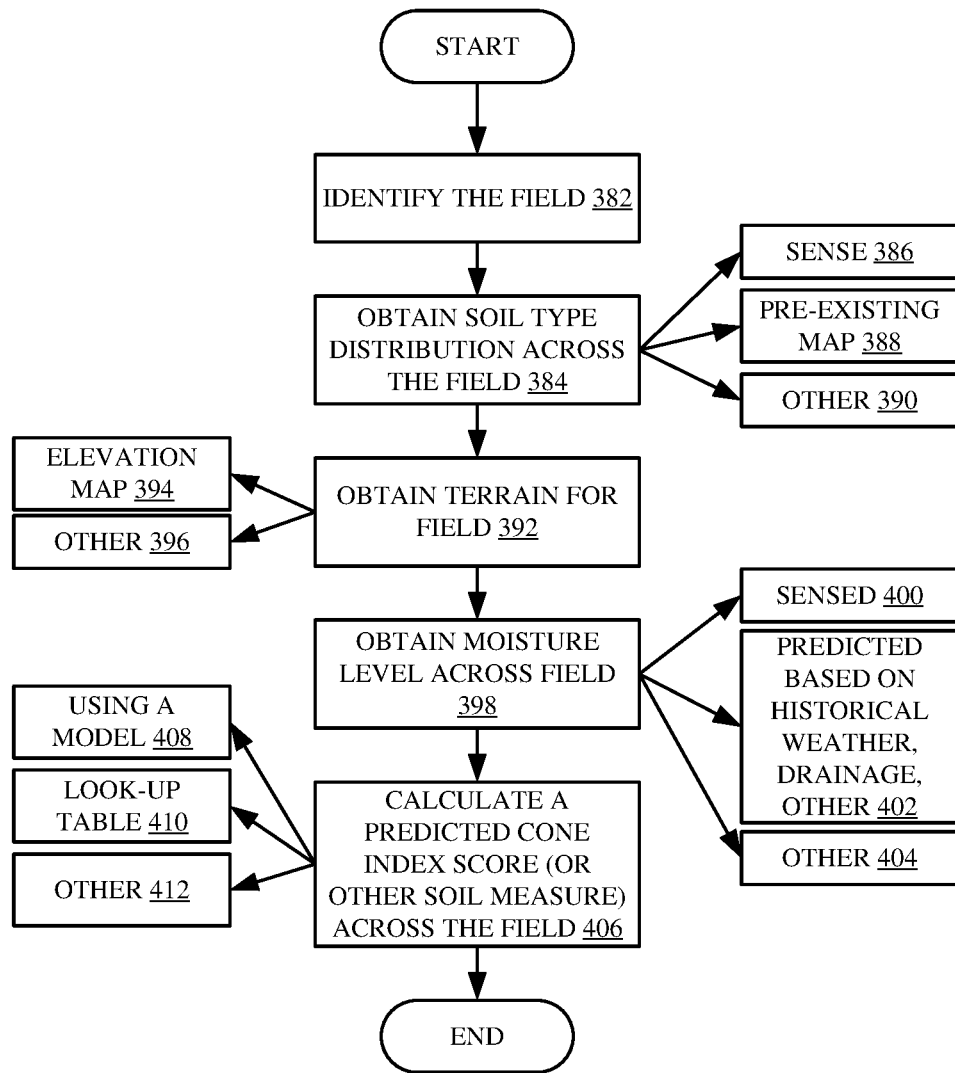
FIG. 5 is a flow diagram illustrating one example of the operation of a soil measure identifying system in predicting a soil cone index or similar measure.

FIG. 5 is a flow diagram illustrating one example of the operation of soil measure prediction system 188 in predicting a soil measure (such as a cone index) for different geographic areas of a field. Soil measure prediction system 188 first identifies the field for which the cone index values are to be predicted, as indicated by block 382 in the flow diagram of FIG. 5.

Soil type identifier 194 then obtains the soil type distribution across the field, as indicated by block 384. The soil type can be sensed by a sensor as indicated by block 386 or it can be obtained from a preexisting map as indicated by block 388, or the soil type can be obtained in other ways as well, as indicated by block 390. Terrain identifier 192 then obtains terrain indicators indicating the terrain (e.g., slope, elevation, etc.) across the field, as indicated by block 392. The terrain can be obtained from an elevation map 394, the terrain can be sensed, or the terrain can be obtained in other ways, as indicated by block 396.

Soil moisture identifier 196 then obtains a moisture level of the soil across the field, as indicated by block 398. The soil moisture level can be sensed by soil moisture sensors, as indicated by block 400, or the soil moisture can be predicted based on historical weather information (such as precipitation information), drainage, and other information, as indicated by block 402. The soil moisture level across the field can be obtained in other ways as well, as indicated by block 404. Score generator 198 then calculates a predicted cone index score (or another soil measure indicative of the ability of the soil to support a load) across the field, as indicated by block 406. Score generator 198 can use a score generation model 408, a lookup table, 410, or any of a wide variety of other mechanisms for calculating a predictive cone index or other soil measure score across the field, based upon the soil type, the terrain, the moisture level and/or any other characteristics, as indicated by block 412.

Figure 6:
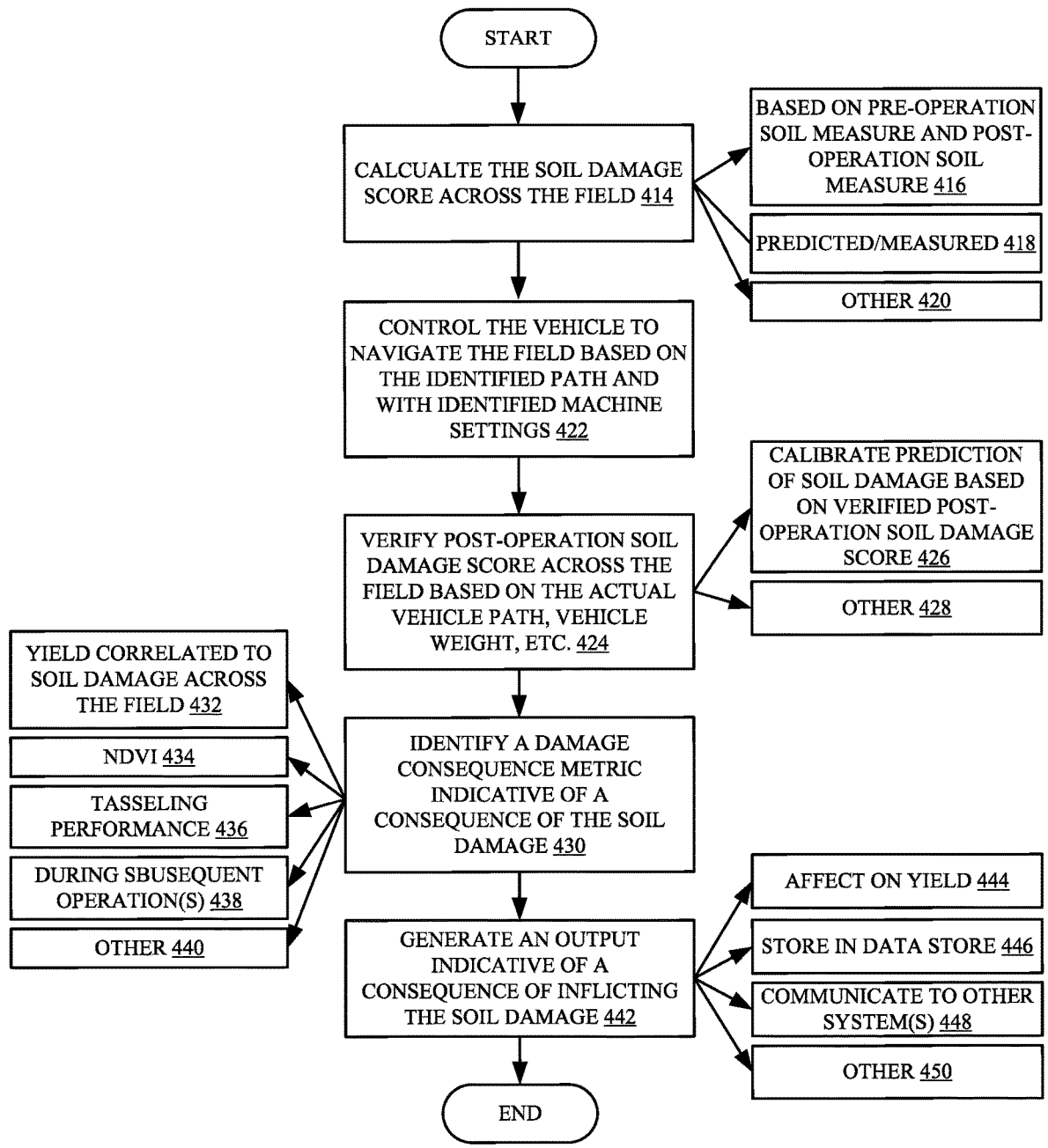
FIG. 6 is a flow diagram illustrating one example of the operation of the soil damage computing system in correlating a soil damage score to a consequence, such as a change in productivity.

FIG. 6 is a flow diagram illustrating one example of how soil damage computing system 110 generates an output indicating the consequences of inflicting predicted or estimated soil damage on the field. If the operator is provided with the potential consequences for inflicting the damage, then the operator may be able to make a more informed choice as to whether to perform the operation, as planned. It is first assumed that soil damage score generation system 146 calculates the soil damage score across the field, as indicated by block 414 in the flow diagram of FIG. 6. The soil damage score may be based on the soil measure calculated by soil measure identification system 148 prior to performing the operation. Also, the soil damage score can be an actually measured score based on the soil measure prior to performing the agricultural operation and the soil measure after performing the operation, as indicated by block 416. The soil damage score across the field can be predicted or measured as indicated by block 418, or it can be calculated in other ways as well, as indicated by block 420.

In the example shown in FIG. 6, control signal generator 154 controls the agricultural machine to travel through the field based on the identified path, with the identified machine settings. Navigating the machine along the recommended path with the machine settings is indicated by block 422 in the flow diagram of FIG. 6. The agricultural machine illustratively is fitted with a cone index penetrometer or another device that can be used to detect the soil measure and vehicle index so that the soil damage score for the different geographic locations in the field can be verified using actual measurements. Verifying the post-operation soil damage score across the field based on the actual vehicle path, the vehicle weight, the soil measure, etc., is indicated by block 424 in the flow diagram of FIG. 6.

The verified soil damage score can be used to calibrate the soil damage score generation system in generating the soil damage score. The verified soil damage score can also be used to calibrate the soil measure prediction system 188 so that the soil measure can be calibrated as well. Calibrating the predicted soil damage score and soil measure based upon the verified post-operation soil damage score is indicated by block 426. The post-operation soil damage score can be obtained in other ways, and used for other processing as well, as indicated by block 428.

Soil damage score output system 178 then identifies a consequence of the damage, as a damage consequence metric, indicative of the consequence of the soil damage. Generating a damage consequence metric is indicated by block 430 in the flow diagram of FIG. 6. For example, the yield can be correlated to the soil damage score across the field to identify a yield loss in areas of the field that are more highly damaged. Identifying the damage consequence metric as the yield correlated to soil damage across the field is indicated by block 432 in the flow diagram of FIG. 6. The damage consequence metric can be correlated to plant health as indicated by normalized difference vegetation index (NDVI) data corresponding to the field, as indicated by block 434.

The damage consequence metric can be a metric that correlates the tasseling performance of corn (or other vegetation performance characteristic) to the soil damage score across the field, or among different fields, as indicated by block 436. The damage consequence metric can be generated during subsequent operations (such as operations later in the season, during subsequent years in the field, or otherwise), as indicated by block 438. The damage consequence metric can be any of a wide variety of other damage consequence metrics obtained in other ways as well, as indicated by block 440.

Soil damage score output system 178 then also generates an output indicative of a consequence of inflicting the soil damage on the field, as indicated by block 442. Again, the consequence can be the affect on yield as indicated by block 444, or any of a wide variety of other outputs. The output indicative of a consequence of inflicting the soil damage can be stored in data store 142 or another data store, as indicated by block 446. The consequence can be communicated to other systems as well, as indicated by block 448. The output indicative of a consequence of inflicting soil damage can be generated in other ways, and be output in other ways as well, as indicated by block 450.

It can thus be seen that the present description provides a mechanism by which soil damage due to driving a heavy machine over a soft field can be measured, predicted, and surfaced for automated control or operator control. The affect or consequence of the soil damage can also be characterized and output. Different settings or mechanisms can be automatically or manually controlled to mitigate predicted soil damage or to avoid operations that will inflict an undesired amount of soil damage on the soil.

The present discussion has mentioned processors and servers. In one example, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. The user interface displays can take a wide variety of different forms and can have a wide variety of different user actuatable input mechanisms disposed thereon. For instance, the user actuatable input mechanisms can be text boxes, check boxes, icons, links, drop-down menus, search boxes, etc. The mechanisms can also be actuated in a wide variety of different ways. For instance, the mechanisms can be actuated using a point and click device (such as a track ball or mouse). The mechanisms can be actuated using hardware buttons, switches, a joystick or keyboard, thumb switches or thumb pads, etc. The mechanisms can also be actuated using a virtual keyboard or other virtual actuators. In addition, where the screen on which the mechanisms are displayed is a touch sensitive screen, the mechanisms can be actuated using touch gestures. Also, where the device that displays them has speech recognition components, the mechanisms can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

It will be noted that the above discussion has described a variety of different systems, components and/or logic. It will be appreciated that such systems, components and/or logic can be comprised of hardware items (such as processors and associated memory, or other processing components, some of which are described below) that perform the functions associated with those systems, components and/or logic. In addition, the systems, components and/or logic can be comprised of software that is loaded into a memory and is subsequently executed by a processor or server, or other computing component, as described below. The systems, components and/or logic can also be comprised of different combinations of hardware, software, firmware, etc., some examples of which are described below. These are only some examples of different structures that can be used to form the systems, components and/or logic described above. Other structures can be used as well.

Figure 7:
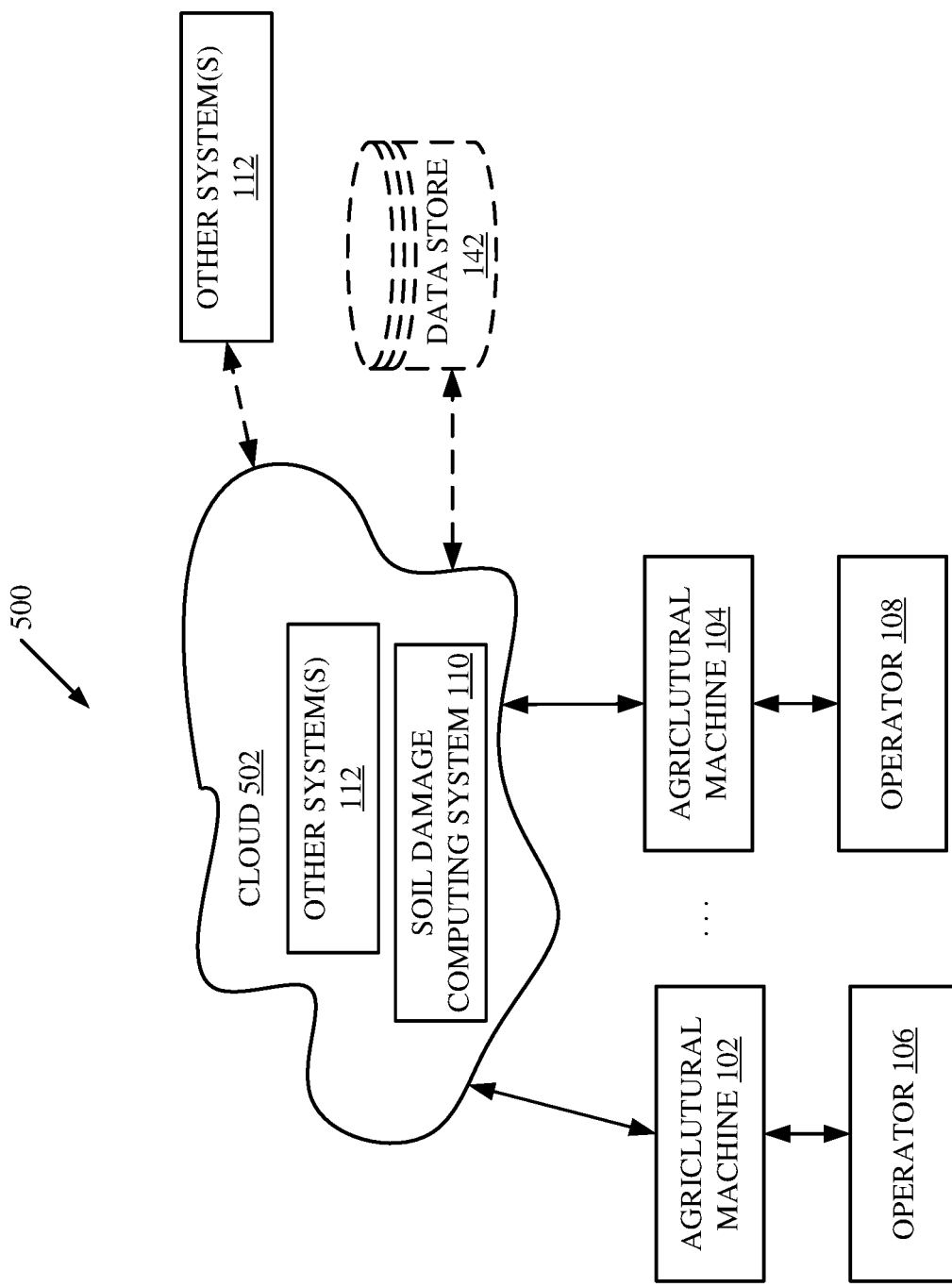
FIG. 7 is a block diagram of one example of the agricultural system deployed in a remote server architecture.

FIG. 7 is a block diagram of agricultural machines 102-104, shown in FIG. 1, except that it communicates with elements in a remote server architecture 500. In an example, remote server architecture 500 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown in previous FIGS. as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, the components and functions can be provided from a conventional server, or the components and functions can be installed on client devices directly, or in other ways.

In the example shown in FIG. 7, some items are similar to those shown in previous FIGS. and they are similarly numbered. FIG. 7 specifically shows that soil damage computing system and data store 142 can be located at a remote server location 502. Therefore, machines 102-104 access those systems through remote server location 502.

FIG. 7 also depicts another example of a remote server architecture. FIG. 7 shows that it is also contemplated that some elements of previous FIGS. are disposed at remote server location 502 while others are not. By way of example, data store 142 or other systems 112 can be disposed at a location separate from location 502, and accessed through the remote server at location 502. Regardless of where the items are located, they can be accessed directly by harvester 100, through a network (either a wide area network or a local area network), the items can be hosted at a remote site by a service, or the items can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another mobile machine (such as a fuel truck) can have an automated information collection system. As the machines 102-104 come close to the fuel truck for fueling, the system automatically collects the information from the machines 102-104 using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the machines 102-104 until the machines 102-104 enter a covered location. The machines 102-104, themselves, can then send the information to the main network.

It will also be noted that the elements of previous FIGS., or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 8:
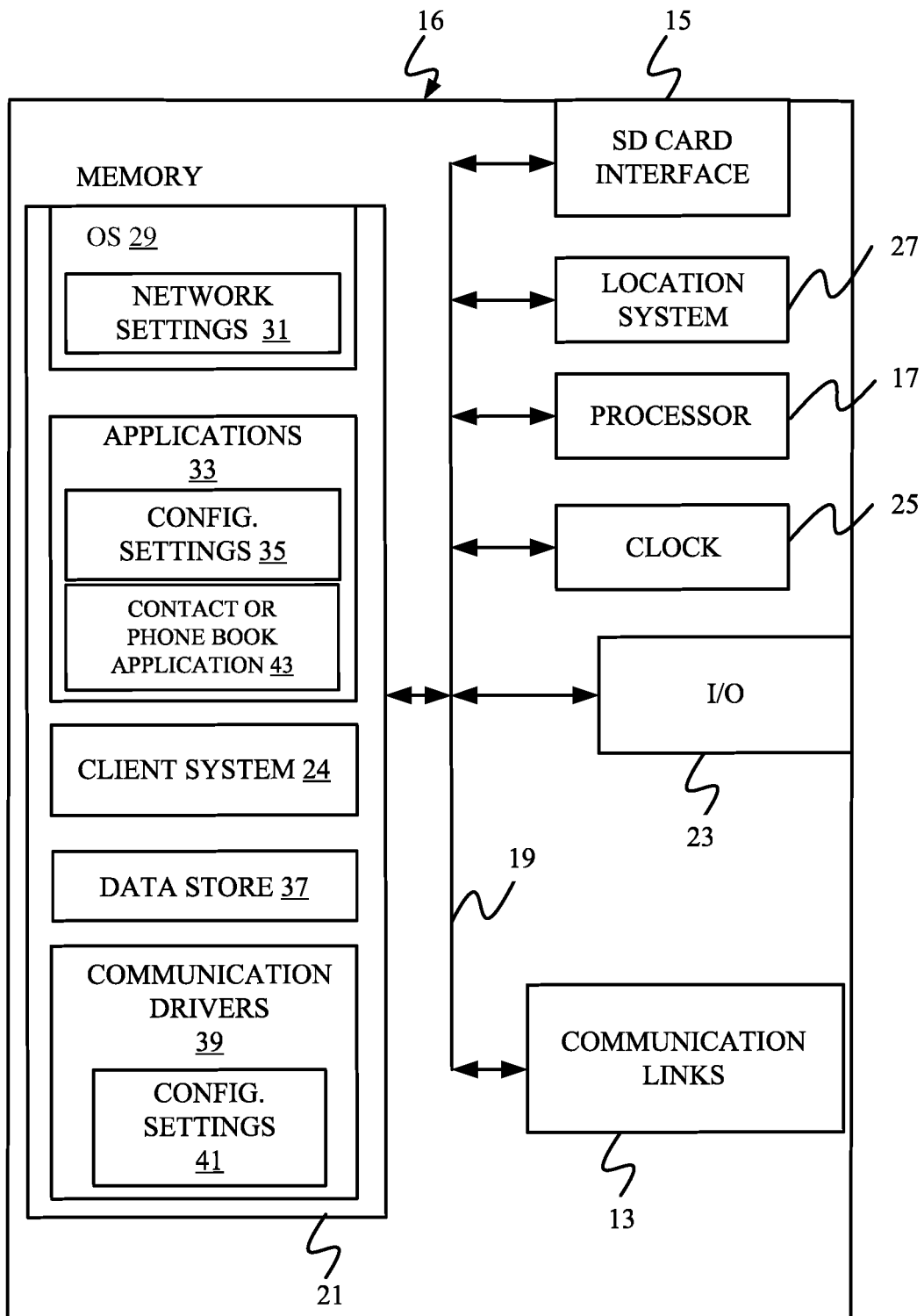
FIGS. 8-10 are block diagrams of mobile devices that can be used in the architectures and systems and machines shown in previous FIGS.
Figure 9:
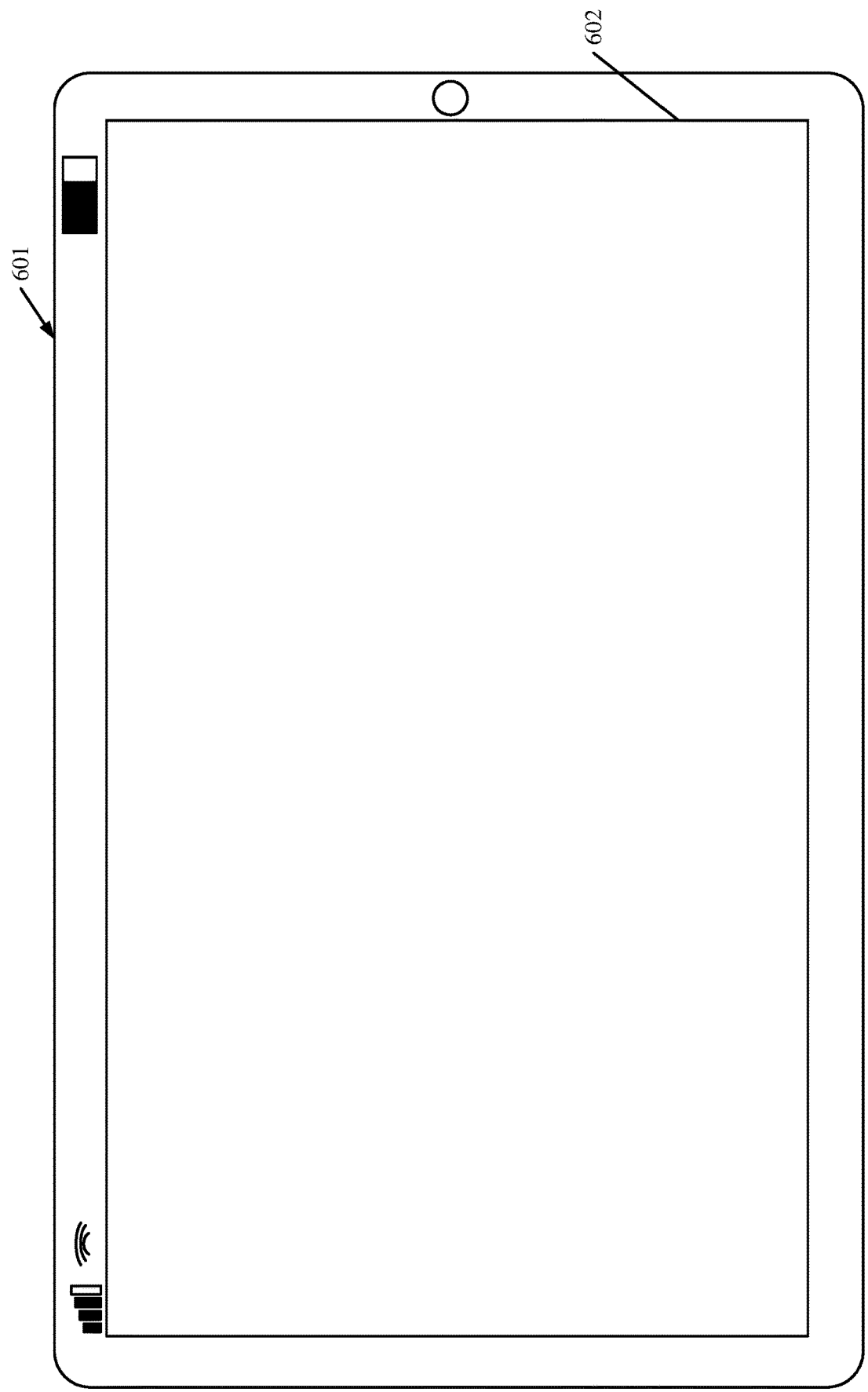
Figure 10:
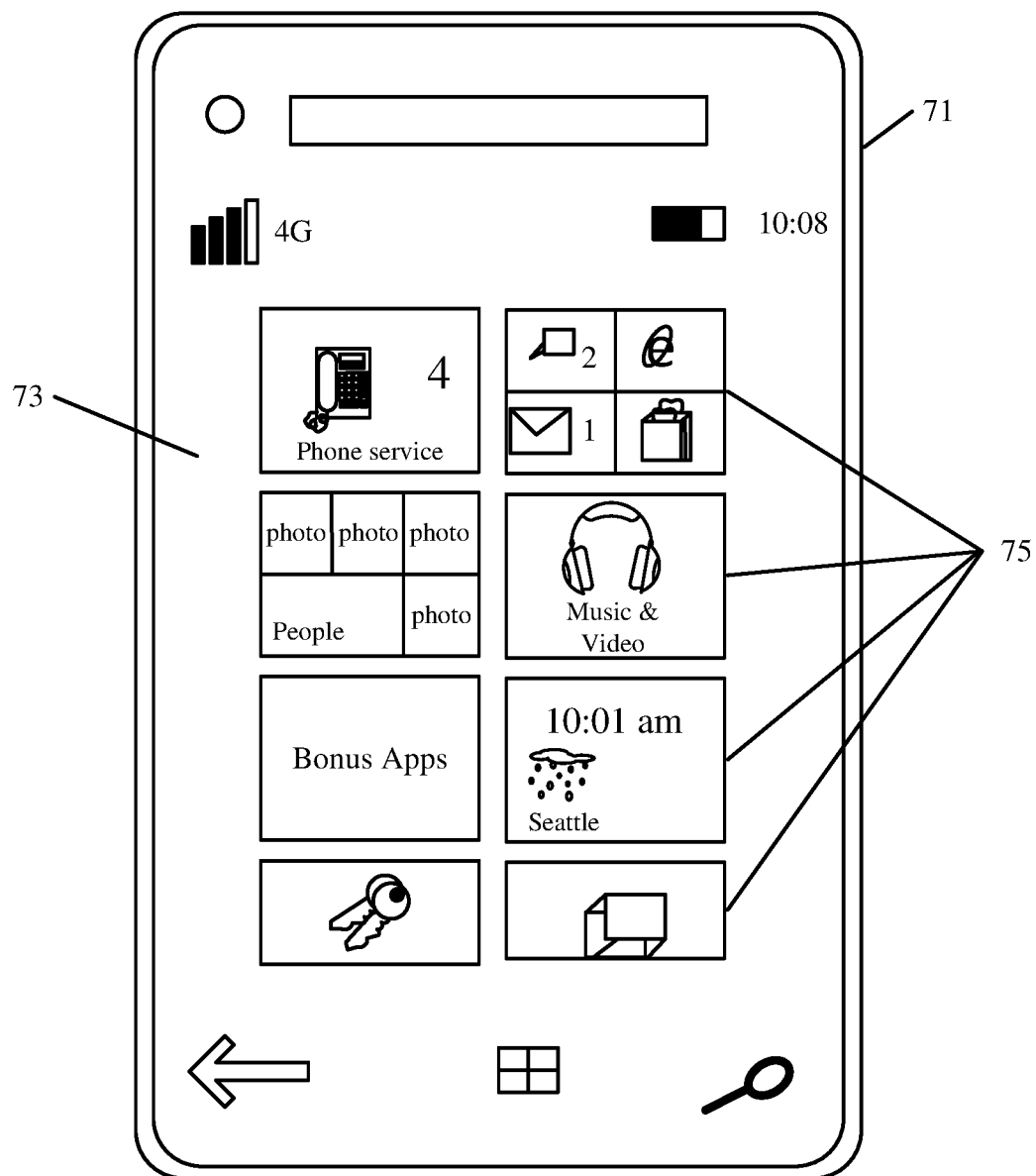

FIG. 8 is a simplified block diagram of one illustrative example of a handheld or mobile computing device that can be used as a user's or client's hand held device 16, in which the present system (or parts of it) can be deployed. For instance, a mobile device can be deployed in the operator compartment of machines 102-104 for use in generating, processing, or displaying the data described above. FIGS. 9-10 are examples of handheld or mobile devices.

FIG. 8 provides a general block diagram of the components of a client device 16 that can run some components shown in previous FIGS., that interacts with them, or both. In the device 16, a communications link 13 is provided that allows the handheld device to communicate with other computing devices and under some examples provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody processors or servers from previous FIGS.) along a bus 19 that is also connected to memory 21 and input/output (I/O) components 23, as well as clock and location system 27.

I/O components 23, in one example, are provided to facilitate input and output operations. I/O components 23 for various examples of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. It can also include computer storage media (described below). Memory 21 stores computer readable instructions that, when executed by processor 17, cause the processor to perform computer-implemented steps or functions according to the instructions. Processor 17 can be activated by other components to facilitate their functionality as well.

FIG. 9 shows one example in which device 16 is a tablet computer 600. In FIG. 9, computer 600 is shown with user interface display screen 602. Screen 602 can be a touch screen or a pen-enabled interface that receives inputs from a pen or stylus. Computer 600 can also use an on-screen virtual keyboard. Of course, computer 600 might also be attached to a keyboard or other user input device through a suitable attachment mechanism, such as a wireless link or USB port, for instance. Computer 600 can also illustratively receive voice inputs as well.

FIG. 10 shows that the device can be a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 11:
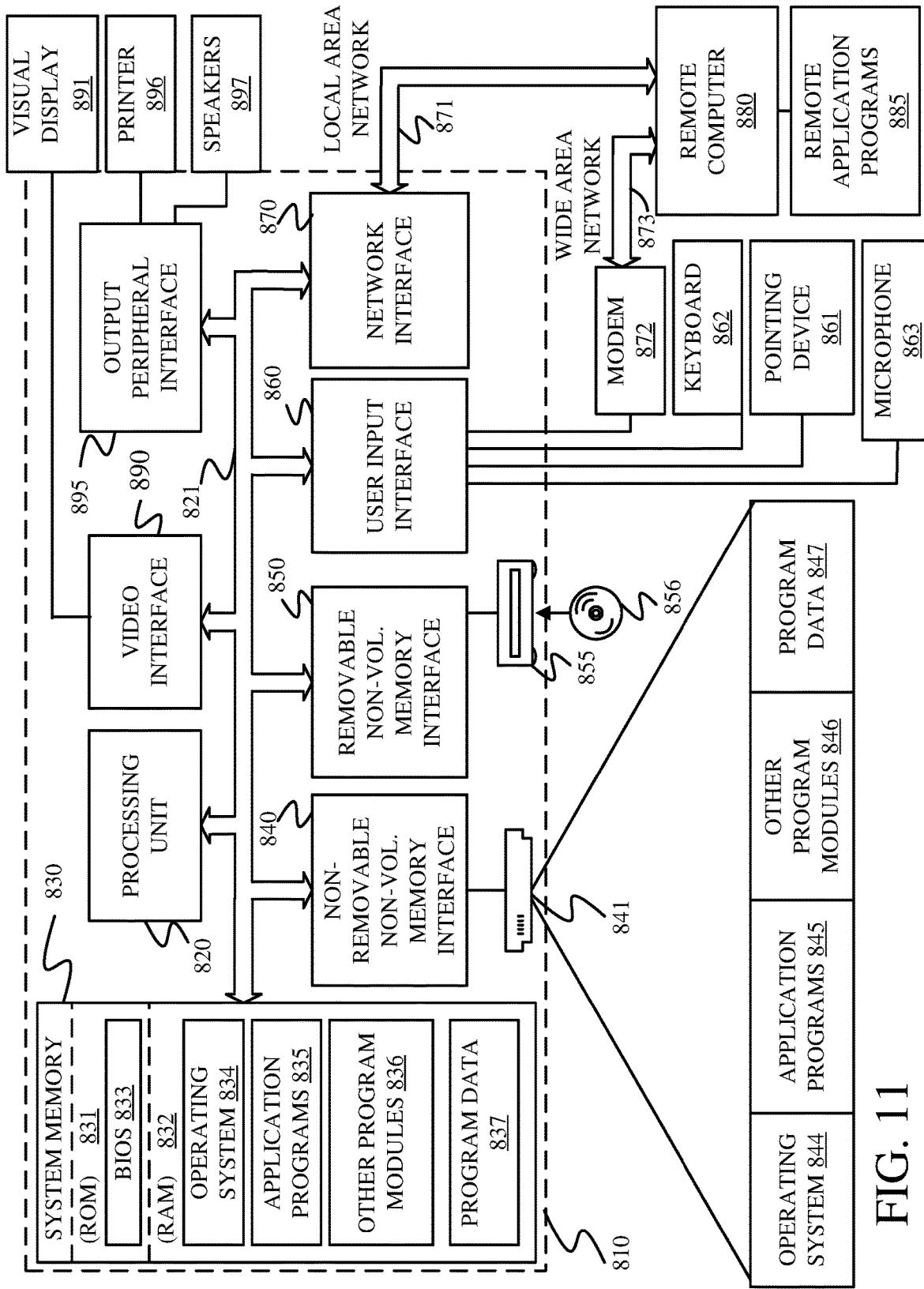
FIG. 11 is a block diagram of one example of a computing environment which can be used in the agricultural system and other systems and machines shown in previous FIGS.

FIG. 11 is one example of a computing environment in which elements of previous FIGS. or parts of it, (for example) can be deployed. With reference to FIG. 11, an example system for implementing some examples includes a general-purpose computing device in the form of a computer 810 programmed to operate as described above. Components of computer 810 may include, but are not limited to, a processing unit 820 (which can comprise processors or servers from previous FIGS.), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to previous FIGS. can be deployed in corresponding portions of FIG. 11.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 11 illustrates operating system 834, application programs 835, other program modules 836, and program data 837.

The computer 810 may also include other removable/non-removable volatile/nonvolatile computer storage media. By way of example only, FIG. 11 illustrates a hard disk drive 841 that reads from or writes to non-removable, nonvolatile magnetic media, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 11, provide storage of computer readable instructions, data structures, program modules and other data for the computer 810. In FIG. 11, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a controller area network—CAN, local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 11 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer implemented method, comprising:
  obtaining a soil measure for soil indicative of an ability of the soil to bear a load;
  obtaining a vehicle index indicative of a force imparted by an agricultural vehicle on the soil, as a load corresponding to the agricultural vehicle varies as the agricultural vehicle travels over the field;
  comparing the soil measure to the vehicle index to obtain a comparison result;
  identifying a soil damage value based on the comparison result; and
  generating a control signal to control the agricultural vehicle based on the soil damage value.

2. The computer implemented method of claim 1 wherein obtaining a soil measure comprises:
  obtaining a plurality of different soil measure values, each soil measure value corresponding to a different geographic location across a field.

3. The computer implemented method of claim 2 wherein obtaining a vehicle index comprises:
  identifying a plurality of different vehicle index values, each vehicle index value corresponding to a different geographic location across the field.

4. The computer implemented method of claim 3 wherein comparing the soil measure to the vehicle index comprises:
  comparing each different soil measure value corresponding to a geographic location to a different vehicle index value corresponding to the geographic location.

5. The computer implemented method of claim 4 wherein identifying a plurality of vehicle index values comprises:
  identifying the plurality of different vehicle index values accounting for the variation in the load as the agricultural vehicle travels along a travel path.

6. The computer implemented method of claim 5 wherein identifying the plurality of different vehicle index comprises:

identifying a set of vehicle characteristics corresponding to the agricultural vehicle; and identifying the plurality of different vehicle index values accounting for the variation in the load as the agricultural vehicle travels along a travel path and based on the vehicle characteristics of the agricultural vehicle.

7. The computer implemented method of claim 2 wherein obtaining a plurality of different soil measure values comprises:

obtaining a map of each of the soil measure values mapped to the different corresponding geographic location.

8. The computer implemented method of claim 2 wherein obtaining a plurality of different soil measure values comprises:

obtaining, as the plurality of different soil measure values, a plurality of different cone index scores.

9. The computer implemented method of claim 2 wherein the agricultural vehicle is a planting machine and wherein obtaining a plurality of different soil measure values comprises:

detecting down force and down force margin on the planting machine; and obtaining, as the plurality of different soil measure values, a plurality of proxy soil measure values based on the detected down force and down force margin.

10. The computer implemented method of claim 2 wherein obtaining a plurality of different soil measure values comprises:

obtaining a set of field characteristics corresponding to the field; and predicting the plurality of different soil measure values based on the set of field characteristics.

11. The computer implemented method of claim 10 wherein obtaining a set of field characteristics comprises:

obtaining terrain data indicative of terrain along a travel path traveled by the agricultural vehicle across the field;

obtaining soil type data indicative of a soil type of the soil along the travel path; and obtaining soil moisture data indicative of soil moisture along the travel path.

12. An agricultural system, comprising:

at least one processor; and a data store that stores computer executable instructions which, when executed by the at least one processor cause the at least one processor to perform steps comprising:

obtaining a soil measure for soil indicative of an ability of the soil to bear a load;

obtaining a vehicle index indicative of a force imparted by an agricultural vehicle on the soil, as a load corresponding to the agricultural vehicle varies as the agricultural vehicle travels over the field;

comparing the soil measure to the vehicle index to obtain a comparison result;

identifying a soil damage value based on the comparison result; and generating a control signal to control the agricultural vehicle based on the soil damage value.

13. The agricultural system of claim 12 wherein obtaining a soil measure comprises:

obtaining a plurality of different soil measure values, each soil measure value corresponding to a different geographic location across a field.

14. The agricultural system of claim 13 wherein obtaining a vehicle index comprises:

identifying a plurality of different vehicle index values, each vehicle index value corresponding to a different geographic location across the field.

15. The agricultural system of claim 14 wherein comparing the soil measure to the vehicle index comprises:

comparing each different soil measure value corresponding to a geographic location to a different vehicle index value corresponding to the geographic location.

16. The agricultural system of claim 15 wherein identifying a plurality of vehicle index values comprises:

identifying the plurality of different vehicle index values accounting for the variation in the load as the agricultural vehicle travels along a travel path.

17. The agricultural system of claim 13 wherein obtaining a plurality of different soil measure values comprises:

obtaining a map of each of the soil measure values mapped to the different corresponding geographic location.

18. The agricultural system of claim 13 wherein obtaining a plurality of different soil measure values comprises:

obtaining a set of field characteristics corresponding to the field; and predicting the plurality of different soil measure values based on the set of field characteristics.

19. A computing system, comprising:

a soil measure identification system obtaining a soil measure for soil indicative of an ability of the soil to bear a load;

a vehicle index identification system obtaining a vehicle index indicative of a force imparted by an agricultural vehicle on the soil, as a load corresponding to the agricultural vehicle varies as the agricultural vehicle travels over the field;

a soil damage score generation system configured to compare the soil measure to the vehicle index to obtain a comparison result and identify a soil damage value based on the comparison result; and a control signal generator generating a control signal to control the agricultural vehicle based on the soil damage value.

20. The computing system of claim 19 wherein the soil measure identification system is configured to obtain a plurality of different soil measure values, each soil measure value corresponding to a different geographic location across a field, wherein the vehicle index identification system is configured to identify a plurality of different vehicle index values, each vehicle index value corresponding to a different geographic location across the field, and wherein the soil damage score generation system is configured to compare each different soil measure value corresponding to a geographic location to a different vehicle index value corresponding to the geographic location.

* * * * *